(12) United States Patent
Derose et al.

(10) Patent No.: US 6,750,378 B2
(45) Date of Patent: Jun. 15, 2004

(54) MAIZE H3C4 PROMOTER COMBINED WITH THE FIRST INTRON OF RICE ACTIN, CHIMERIC GENE COMPRISING IT AND TRANSFORMED PLANT

(75) Inventors: Richard Derose, Lyons (FR); Georges Freyssinet, Cyr Au Mont d'Or (FR)

(73) Assignee: Rhone-Poulenc Agro, Lyons (FR)

( * ) Notice: Subject to any disclaimer, the term of this patent is extended or adjusted under 35 U.S.C. 154(b) by 0 days.

(21) Appl. No.: 09/037,531

(22) Filed: Mar. 10, 1998

(65) Prior Publication Data
US 2002/0104117 A1 Aug. 1, 2002

(30) Foreign Application Priority Data
Dec. 14, 1997 (FR) .............................. 97 16726

(51) Int. Cl.$^7$ ..................... C12N 15/09; C12N 15/29; C12N 15/82; A01H 5/00; A01H 1/00
(52) U.S. Cl. ................ 800/278; 800/287; 800/279; 800/320; 800/320.1; 800/300; 800/302; 435/320.1; 435/419; 435/468; 435/418; 536/23.1; 536/23.2; 536/23.6; 536/24.1
(58) Field of Search .................. 800/278, 287, 800/320, 320.1, 279, 300, 302; 435/320.1, 418, 419, 468; 536/23.1, 24.1, 23.2

(56) References Cited

U.S. PATENT DOCUMENTS

| | | | |
|---|---|---|---|
| 5,510,471 A | 4/1996 | Lebrun et al. | 536/23.4 |
| 5,635,618 A | 6/1997 | Capellades et al. | 536/24.1 |

FOREIGN PATENT DOCUMENTS

| | | |
|---|---|---|
| EP | 508909 | 10/1992 |
| EP | 652286 | 5/1995 |
| WO | 91/09948 | 7/1991 |
| WO | 92/04449 | 3/1992 |
| WO | 97/04103 | 2/1997 |

OTHER PUBLICATIONS

Kim et al. Plant Molecular Biology, 1994, vol. 24, pp. 105–117.*
Benfey et al. Science, 1990, vol 250, pp. 959–966.*
The Plant Journal (1993) 3(2), 241–252, "A wheat histone H3 promoter confers cell division–dependent . . . gene in transgenic rice plants", Terada et al.
Plant Science, 89 (1993), 177–184, "Replication–independent cis–acting element of a maize histone gene promoter", Marc Lepetit et al.
Mol Gen. Genet (1989) 219:404–412, "Organization of the histone H3 and H4 multgenic families in maize and in relate genomes", Nicole Chaubet et al.
Plant Molecular Biology, 22: 1007–1015, 1993, "Nuclease sensitivity and functional analysis of a maize histone H3 gene promoter", Pierre Brignon et al.
Plant Molecular Biology 22: 1007–1015, 1993, "Nuclease sensitivity and functional analysis of a maize histone H3 gene promoter", Brignon et al.

* cited by examiner

*Primary Examiner*—Amy J. Nelson
*Assistant Examiner*—Medina A. Ibrahim
(74) *Attorney, Agent, or Firm*—Connolly Bove Lodge & Hutz LLP

(57) ABSTRACT

The present invention relates to a DNA sequence, a 5' regulatory element allowing the expression of a heterologous gene in a plant cell from a monocotyledonous plant, characterized in that it comprises, in the direction of transcription, a first DNA sequence, which is a functional fragment of the sequence of the maize H3C4 promoter, and a second DNA sequence, which is a functional fragment of the sequence of the first intron of rice actin.

The invention also relates to a chimeric gene comprising the said DNA sequence and the plants transformed with the said gene.

22 Claims, 1 Drawing Sheet

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 1021 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
CTTATGTGCA CCATTTACTG TAATGCATAA TCATTTAATT GAATAGCAAA CTTTTCTATT      60

ACTTCTTTAC TAACATAATT CTTGGTTTTA AAATTCAGTC CTCAACATTC ATTGCTAAG      120

TATAAGTTGA GACTGTCAAA ATTTACTATT TTATTTCTTC ATATTTTTTT TCCTTATACA     180

CATTTTGGGC CTTACAATCC ATCATCTATA TCCATCCTTT CCGGTGTCCT CTAAAAGATT    240

CCATCCTCTG AATCTTATTC CTCTCCAATA ACGTTCTCTA AATCAGGTCT CTATAAGCAA    300

TACCTATATT AGAGACATTT TTTATTTTTT GTACATACAT ATTTGTCATA CTCTCAAATG    360

CATTATACAT ATTTAGTTTT ACTAAACCGA TTATTTAAAG TATTCAAACG GATGAAGAAC    420

TGTTTAGATA AATTCTATAT ATAGAGAATC CAGTAGCGTT CTCTAAATTT AGATGATTAT    480

TTAGAGGACG CTGTTAGAAA ACGTAAAAAA TTCTTTGATT ATTTATATTT AGGGTAGAGT    540
```

-continued

```
AGCCTTTATG CTTTATAGAT CTTTGGTGGA CCCAGCCTTA TACCGGTTAT TTTCGCGATT      600

GCGCCTCTCA TTTTCACTCC AGCGCCCCAC ATTTTCACGT TTTCACCGAA GCGCCCAGCC      660

TGCCTAACCA ACAAATTGGT ACGGTGGCGC GGTTTTCAAA AGAAGTCGGA AACCATCTGC      720

ACCCACCGAC TAGTAGGCCC TCGGATCCTC CCTGATTAAG TCCTAGCCAA TAGGAGCCCA      780

GAACCACCCA TCACGCGGAT CGTCCCTACG CTTCCACCTC ATCGGCGCCG TCCATCTCCA      840

TCCAACACCT ATTCCGTTAC CTTGCCCATC CTCCGAAAAA ATTCTCGGCT CGCGCTCCGC      900

ACCTACTACA AATACCCATC CCATCACGAC GCATCGCATC ACTGCCAAAT CCCCCAGAAA      960

ATCAACACCT CCCAATTCCA CGCTGCCACC AACTCGCCGT CCTCCGCGCC AAGCACCAAA     1020

G                                                                    1021
```

(2) INFORMATION FOR SEQ ID NO:2:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
GTAACCACCC CGCCCCTCTC CTCTTTCTTT CTCCGTTTTT TTTTTCGTCT CGGTCTCGAT       60

CTTTGGCCTT GGTAGTTTGG GTGGGCGAGA GCGGCTTCGT CGCCCAGATC GGTGCGCGGG      120

AGGGGCGGGA TCTCGCGGCT GGCGTCTCCG GGCGTGAGTC GGCCCGGATC CTCGCGGGGA      180

ATGGGGCTCT CGGATGTAGA TCTGATCCGC CGTTGTTGGG GGAGATGATG GGGCGTTTAA      240

AATTTCGCCA TGCTAAACAA GATCAGGAAG AGGGGAAAAG GGCACTATGG TTTATATTTT      300

TATATATTTC TGCTGCTGCT CGTCAGGCTT AGATGTGCTA GATCTTTCTT TCTTCTTTTT      360

GTGGGTAGAA TTTGAATCCC TCAGCATTGT TCATCGGTAG TTTTTCTTTT CATGATTTGT      420

GACAAATGCA GCCTCGTGCG GAGCTTTTTT GTAG                                 454
```

(2) INFORMATION FOR SEQ ID NO:3:

(i) SEQUENCE CHARACTERISTICS:
        (A) LENGTH: 1565 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GAATTCCTGC AGGTCGACGG ATCCCCCTTA TGTGCACCAT TTACTGTAAT GCATAATCAT       60

TTAATTGAAT AGCAAACTTT TCTATTACTT CTTTACTAAC ATAATTCTTG GTTTTAAAAT      120

TCAGTCCTCA ACATTCATTG CTCAAGTATA AGTTGAGACT GTCAAAATTT ACTATTTTAT      180

TTCTTCATAT TTTTTTTCCT TATACACATT TTGGGCCTTA CAATCCATCA TCTATATCCA      240

TCCTTTCCGG TGTCCTCTAA AAGATTCCAT CCTCTGAATC TTATTCCTCT CCAATAACGT      300

TCTCTAAATC AGGTCTCTAT AAGCAATACC TATATTAGAG ACATTTTTTA TTTTTTGTAC      360

ATACATATTT GTCATACTCT CAAATGCATT ATACATATTT AGTTTACTA AACCGATTAT       420

TTAAAGTATT CAAACGGATG AAGAACTGTT TAGATAAATT CTATATATAG AGAATCCAGT      480

AGCGTTCTCT AAATTTAGAT GATTATTTAG AGGACGCTGT TAGAAAACGT AAAAAATTCT      540
```

-continued

```
TTGATTATTT ATATTTAGGG TAGAGTAGCC TTTATGCTTT ATAGATCTTT GGTGGACCCA      600

GCCTTATACC GGTTATTTTC GCGATTGCGC CTCTCATTTT CACTCCAGCG CCCCACATTT      660

TCACGTTTTC ACCGAAGCGC CCAGCCTGCC TAACCAACAA ATTGGTACGG TGGCGCGGTT      720

TTCAAAAGAA GTCGGAAACC ATCTGCACCC ACCGACTAGT AGGCCCTCGG ATCCTCCCTG      780

ATTAAGTCCT AGCCAATAGG AGCCCAGAAC CACCCATCAC GCGGATCGTC CCTACGCTTC      840

CACCTCATCG GCGCCGTCCA TCTCCATCCA ACACCTATTC CGTTACCTTG CCCATCCTCC      900

GAAAAAATTC TCGGCTCGCG CTCCGCACCT ACTACAAATA CCCATCCCAT CACGACGCAT      960

CGCATCACTG CCAAATCCCC CAGAAAATCA ACACCTCCCA ATTCCACGCT GCCACCAACT     1020

CGCCGTCCTC CGCGCCAAGC ACCAAAGGAA TTGGCCGCCA CCGCGGTGGA GCTCCTCCCC     1080

CCTCCCCCTC CGCCGCCGCC GGTAACCACC CCGCCCCTCT CCTCTTTCTT TCTCCGTTTT     1140

TTTTTTCGTC TCGGTCTCGA TCTTTGGCCT TGGTAGTTTG GGTGGGCGAG AGCGGCTTCG     1200

TCGCCCAGAT CGGTGCGCGG GAGGGGCGGG ATCTCGCGGC TGGCGTCTCC GGGCGTGAGT     1260

CGGCCCGGAT CCTCGCGGGG AATGGGGCTC TCGGATGTAG ATCTGATCCG CCGTTGTTGG     1320

GGGAGATGAT GGGGCGTTTA AAATTTCGCC ATGCTAAACA AGATCAGGAA GAGGGGAAAA     1380

GGGCACTATG GTTTATATTT TTATATATTT CTGCTGCTGC TCGTCAGGCT TAGATGTGCT     1440

AGATCTTTCT TTCTTCTTTT TGTGGGTAGA ATTTGAATCC CTCAGCATTG TTCATCGGTA     1500

GTTTTTCTTT TCATGATTTG TGACAAATGC AGCCTCGTGC GGAGCTTTTT TGTAGGTAGA     1560

CCATG                                                                 1565

(2) INFORMATION FOR SEQ ID NO:4:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGGGCCCCCT AGGGTTTAAA CGGCCAGTCA GGCCGAATTC GAGCTCGGTA CCCGGGGATC       60

CTCTAGAGTC GACCTGCAGG CATGC                                            85

(2) INFORMATION FOR SEQ ID NO:5:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CCCTGAACCA GGCTCGAGGG CGCGCCTTAA TTAAAAGCTT GCATGCCTGC AGGTCGACTC       60

TAGAGG                                                                 66
```

MAIZE H3C4 PROMOTER COMBINED WITH THE FIRST INTRON OF RICE ACTIN, CHIMERIC GENE COMPRISING IT AND TRANSFORMED PLANT

The present invention relates to a new 5' regulatory sequence allowing the expression, in monocotyledonous plants, of a sequence heterologous to the said regulatory sequence, encoding a protein of interest. The present invention also relates to a chimeric gene comprising the said regulatory sequence, a heterologous sequence encoding a protein of interest and a 3' regulatory sequence allowing the expression of the protein of interest in a plant cell from a monocotyledonous plant, as well as a transformed monocotyledonous plant comprising the said chimeric gene and the means necessary for the transformation of plant cells and of plants.

Various promoters allowing the expression of sequences encoding proteins of interest in plants are known, are described in the literature, and have already allowed the development, to a commercial stage, of plants modified by genetic engineering. They are promoter sequences of genes which are expressed naturally in plants, in particular promoters of bacterial, viral or plant origin such as, for example, that of a gene for the ribulose bisphosphate carboxylase/oxygenase small subunit (U.S. Pat. No. 4,962,028) or of a gene of a plant virus such as, for example, that of cauliflower mosaic (U.S. Pat. No. 5,352,605). Promoters allowing the expression of heterologous genes in plants are in particular described in the following patents and patent applications: U.S. Pat. No. 5,086,169, EP 0 353 908, U.S. Pat. Nos. 5,139,954, 5,378,619, 5,563,328, 5,589,583, 5,633,363, 5,633,439, 5,633,440, 5,633,447, 5,635,618, 5,639,948 and 5,639,952.

However, some of these promoters, and more particularly the promoters of plant origin, are not functional in monocotyledonous plants.

Arabidopsis sp. histone promoters described in patent application EP 0,507,698 are for example known which are particularly efficient for allowing the expression of a heterologous gene in dicotyledonous plants such as tobacco, oil seed rape or soya bean, which are not functional in monocotyledonous plants such as maize.

The rice actin promoter is a promoter known to allow the expression of heterologous genes in monocotyledonous plants (U.S. Pat. No. 5,641,876). However, the problem of identifying new functional 5' regulatory sequences for the expression of heterologous sequences in monocotyledonous plants still remains.

The present invention relates to a new DNA sequence, a 5' regulatory element allowing the expression of a heterologous gene in a plant cell from a monocotyledonous plant, the said DNA sequence comprising, in the direction of transcription, a first DNA sequence, which is a functional fragment of the sequence of the maize H3C4 promoter, and a second DNA sequence, which is a functional fragment of the sequence of the first intron of rice actin.

Figure 1:
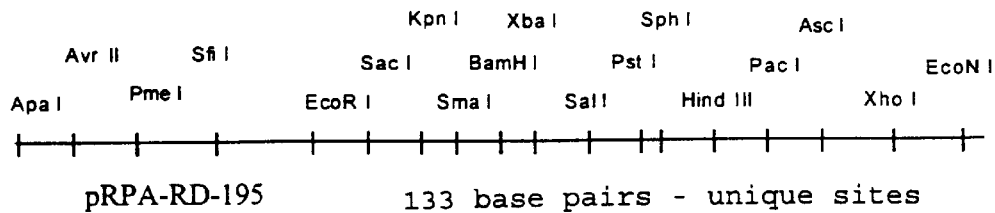
FIG. 1 shows the multiple cloning site of the cloning vector pRPA-RD-195.

The sequence of the maize H3C4 promoter is in particular described by Brignon et al. (Plant. Mol. Biol., 22: 1007–1015, 1993). It is the AluI fragment of the maize H3C4 promoter, of about 1 kb, corresponding to bases −7 to −1029 relative to the ATG of the sequence encoding the maize histone H3C4.

The sequence of the first intron of rice actin is in particular described in patent U.S. Pat No. 5,641,876.

Functional fragment is understood according to the invention to mean any DNA sequence derived from the sequence of the maize H3C4 promoter or from the sequence of the first intron of rice actin, which reproduces the function of the sequence from which it is derived.

According to one embodiment of the invention, the functional fragment of the sequence of the maize H3C4 promoter comprises the DNA sequence described by the sequence identifier No. 1 (SEQ ID NO: 1) or a sequence homologous to the said sequence. Preferably, the functional fragment of the sequence of the maize H3C4 promoter consists of the DNA sequence described by the sequence identifier No. 1.

According to one embodiment of the invention, the functional fragment of the first intron of rice actin comprises the DNA sequence described by the sequence identifier No. 2 (SEQ ID NO: 2) or a sequence homologous to the said sequence. Preferably, the functional fragment of the first intron of rice actin consists of the DNA sequence described by the sequence identifier No. 2.

The DNA sequence, a 5' regulatory element, according to the invention may comprise, in addition, between the first and second DNA sequences, neutral DNA fragments which are generally necessary for the construction of the sequence according to the invention. These are DNA fragments comprising up to 30 base pairs, preferably up to 20 base pairs. Neutral DNA fragments are understood according to the invention to mean DNA fragments which do not substantially modify the respective functions of the first and second DNA sequences of the sequence according to the invention.

According to a preferred embodiment of the invention, the DNA sequence according to the invention comprises the DNA sequence represented by the sequence identifier No. 3 (SEQ ID NO: 3) or a sequence homologous to the said sequence. More preferably, the sequence according to the invention consists of the DNA sequence represented by the sequence identifier No. 3.

"Homologue" is understood according to the invention to mean a DNA sequence representing one or more sequence modifications relative to the reference DNA sequence described by the sequence identifier No. 1, 2 or 3, and reproducing the function of the abovementioned sequences. These modifications may be obtained according to the customary mutation techniques, or alternatively by choosing the synthetic oligonucleotides which may be used in the preparation of the said sequence by hybridization. Advantageously, the degree of homology will be at least 70% relative to the reference sequence, preferably at least 80%, more preferably at least 90%.

The present invention also relates to a chimeric gene (or an expression cassette) comprising a coding sequence as well as heterologous regulatory elements at the 5' and 3' positions capable of functioning in plant cells from monocotyledonous plants, in which the 5' regulatory elements comprise the DNA sequence according to the invention defined above.

"Plant cell" is understood to mean according to the invention any cell derived from a monocotyledonous plant and capable of constituting undifferentiated tissues such as calli, differentiated tissues such as embryos, monocotyledonous plant portions, monocotyledonous plants or seeds.

"Monocotyledonous plant" is understood according to the invention to mean any differentiated multicellular organism capable of photosynthesis, more particularly crop plants intended or otherwise as animal feed or for human consumption, such as for example wheat, barley, oats, rice, maize, sorghum, sugar cane and the like.

According to the invention, it is also possible to use, in combination with the regulatory promoter sequence according to the invention, other regulatory sequences, which are situated between the promoter and the coding sequence, such as the sequences encoding transit peptides, either single, or double, and in this case optionally separated by an intermediate sequence, that is to say comprising, in the direction of transcription, a sequence encoding a transit peptide for a plant gene encoding a plastid localization enzyme, a portion of sequence of the mature N-terminal portion of a plant gene encoding a plastid localization enzyme, and then a sequence encoding a second transit peptide for a plant gene encoding a plastid localization enzyme consisting of a portion of sequence of the mature N-terminal portion of a plant gene encoding a plastid localization enzyme, as described in application EP 0,508,909. As transit peptide, there may also be mentioned the signal peptide for the tobacco PR-1a gene described by Cornelissen et al.

As regulatory terminator or polyadenylation sequence, there may be used any corresponding sequence of bacterial origin, such as for example the *Agrobacterium tumefaciens* nos terminator, or alternatively of plant origin, such as for example a histone terminator as described in application EP 0,633,317.

The coding sequence of the chimeric gene according to the invention may comprise any sequence encoding the protein of interest which it is desired to express in a plant cell or a monocotyledonous plant.

This may be a gene encoding a selectable marker such as a gene conferring on the transformed monocotyledonous plant new agronomic properties, or a gene for enhancing the agronomic quality of the transformed monocotyledonous plant.

Among the genes encoding selectable markers, there may be mentioned genes for resistance to antibiotics, genes for tolerance to herbicides (bialaphos, glyphosate or isoxazoles), genes encoding easily identifiable enzymes such as the enzyme GUS, genes encoding pigments or enzymes regulating the production of pigments in the transformed cells. Such selectable marker genes are in particular described in patent applications WO 91/02071 and WO 95/06128.

Among the genes conferring new agronomic properties on transformed monocotyledonous plants, there may be mentioned the genes conferring tolerance to certain herbicides, those conferring tolerance to certain insects, those conferring tolerance to certain diseases and the like. Such genes are in particular described in patent applications WO 91/02071 and WO 95/06128.

As regulatory terminator or polyadenylation sequence, there may be used any corresponding sequence of bacterial origin, such as for example the *Agrobacterium tumefaciens* nos terminator, or alternatively of plant origin, such as for example a histone terminator as described in application EP 0,633317.

The present invention is particularly appropriate for the expression of genes conferring tolerance to certain herbicides on transformed plant cells and on transformed monocotyledonous plants. Among the genes conferring tolerance to certain herbicides, there may be mentioned the Bar gene conferring tolerance to bialaphos, the gene encoding an appropriate EPSPS conferring resistance to herbicides having EPSPS as target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435, FR 2,736,926), the gene encoding glyphosate oxydoreductase (U.S. Pat. No. 5,463,175), or alternatively a gene encoding an HPPD conferring tolerance to herbicides having HPPD as target, such as the isoxazoles, in particular isoxafutole (FR 95 06800, FR 95 13570), the diketonitriles (EP 496 630, EP 496 631) or the triketones, in particular sulcotrione (EP 625 505, EP 625 508, U.S. Pat. No. 5,506,195). Such genes encoding an HPPD conferring tolerance to herbicides having HPPD as target are described in patent application WO 96/38567 and in unpublished patent application FR 97 14264, filed on Nov. 7, 1997, whose content is incorporated herein by reference.

Among the genes encoding an appropriate EPSPS conferring resistance to herbicides having EPSPS as target, there may be mentioned more particularly the gene encoding a plant EPSPS, in particular from maize, having two mutations 102 and 106, which is described in patent application FR 2,736,926, called hereinafter double-mutant EPSPS, or alternatively the gene encoding an EPSPS isolated from Agrobacterium which is described by the sequences ID 2 and ID 3 of patent U.S. Pat. No. 5,633,435, called hereinafter CP4.

Among the genes encoding an HPPD conferring tolerance to herbicides having HPPD as target, there may be mentioned more particularly the HPPD from Pseudomonas and that from Arabidopsis, which are described in patent application WO 96/38567.

In the case of the genes encoding EPSPS or HPPD, and more particularly for the above genes, the sequence encoding these enzymes is advantageously preceded by a sequence encoding a transit peptide, in particular the transit peptide called optimized transit peptide described in patents U.S. Pat. No. 5,510,471 or U.S. Pat. No. 5,633,448 whose content is incorporated herein by reference.

According to a preferred embodiment of the invention, the chimeric gene according to the invention comprises, in the direction of transcription, a 5' regulatory sequence according to the invention as defined above, functionally linked to a sequence encoding a fusion protein transit peptide/protein of interest, functionally linked to a 3' regulatory sequence, the different elements of the chimeric gene being defined above, the protein of interest being preferably an enzyme conferring tolerance to certain herbicides, more preferably enzymes of the EPSPS or HPPD type defined above.

Sequences encoding fusion proteins transit peptide/EPSPS, and more particularly OTP/double-mutant EPSPS are in particular described in U.S. Pat. Nos. 4,940,835, 5,633,448 and FR 2 736 926.

For the fusion protein OTP/CP4, persons skilled in the art will know how to construct the corresponding gene by taking the sequence encoding the CP4 described in patent U.S. Pat. No. 5,633,435 and by following the procedure described in patents U.S. Pat. Nos. 4,940,835, 5,633,448 and FR 2,736,926 or in the examples below. The present invention also relates to a chimeric gene comprising, in the direction of transcription, an appropriate 5' regulatory sequence to ensure the expression of a heterologous gene in a plant cell, functionally linked to a sequence encoding a fusion protein OTP/CP4, functionally linked to a 3' regulatory sequence. The 5' regulatory elements comprise not only the 5' regulatory elements according to the invention defined above, but also all the appropriate regulatory elements for allowing the expression of heterologous genes in plant cells from monocotyledonous or dicotyledonous plants which are known to a person skilled in the art or of the future, and in particular those described above.

The sequences encoding fusion proteins transit peptide/HPPD are described in patent application WO 96/38567.

The present invention also relates to a cloning or expression vector for the transformation of a plant cell or of a monocotyledonous plant, the transformed plant cells and plants containing at least one chimeric gene as defined above. The vector according to the invention comprises, in addition to the above chimeric gene, at least one replication origin. This vector may consist of a plasmid, a cosmid, a bacteriophage or a virus, which are transformed by introducing the chimeric gene according to the invention. Such vectors for transforming plant cells and monocotyledonous plants are well known to a person skilled in the art and are widely described in the literature. Preferably, the vector for transforming plant cells or plants according to the invention is a plasmid.

The subject of the invention is also a method of transforming plant cells by integrating at least one nucleic acid fragment or a chimeric gene as defined above, which transformation may be obtained by any appropriate known means with the vector according to the invention.

A series of methods consists in bombarding cells or cellular tissues with particles to which DNA sequences are attached. Another series of methods consists in using, as means of transfer into the plant, a chimeric gene inserted into an *Agrobacterium tumefaciens* Ti plasmid or an *Agrobacterium rhizogenes* Ri plasmid. Other methods may be used, such as microinjection or electroporation, or alternatively direct precipitation by means of PEG.

Persons skilled in the art will choose the appropriate method according to the nature of the plant cell or of the plant.

The subject of the present invention is also the plant cells or plants transformed and which contain at least one chimeric gene according to the invention defined above.

The subject of the present invention is also the plants containing transformed cells, in particular the plants regenerated from transformed cells. The regeneration is obtained by any appropriate method which depends on the nature of the species.

For the methods of transforming plant cells and of regenerating monocotyledonous plants, there may be mentioned in particular Gordon-Kamm, W. J. et al. (*Transformation of Maize Cells and Regeneration of Fertile Transgenic Plants*, The Plant Cell, vol. 2, 603–618, July 1990), whose content is incorporated herein by reference, and the following patents and patent applications: U.S. Pat. Nos. 5,177,010, 5,187,073, EP 267,159, EP 604 662, EP 672 752, U.S. Pat. Nos. 4,945,050, 5,036,006, 5,100,792, 5,371,014, 5,478, 744, 5,484,956, 5,508,468, 5,538,877, 5,554,798, 5,489,520, 5,510,318, 5,204,253, 5,405,765, EP 442 174, EP 486 233, EP 486 234, EP 539 563, EP 674 725, WO 91/02071 and WO 95/06128.

The present invention also relates to the transformed plants derived from the culture and/or the crossing of the above regenerated plants, as well as the seeds of transformed plants.

In the case where the chimeric gene according to the invention comprises a sequence encoding an enzyme conferring tolerance to a particular herbicide, the present invention also relates to a method of controlling weed in an area of a field comprising seeds or plants transformed with the said chimeric gene according to the invention, which method consists in applying to the said area of the field a dose of the said particular herbicide which is toxic to the said weed, without, however, substantially affecting the seeds or plants transformed with the said chimeric gene according to the invention comprising the said sequence encoding an enzyme conferring tolerance to the said particular herbicide.

The present invention also relates to a method of culturing the plants transformed according to the invention with a chimeric gene according to the invention comprising a sequence encoding an enzyme conferring tolerance to a particular herbicide defined above, which method consists in planting the seeds of the said transformed plants in an area of a field which is appropriate for the culture of the said plants, in applying to the said area of the said field a dose of the said particular herbicide which is toxic to weeds should weeds be present, without substantially affecting the said seeds or the said transformed plants, and then in harvesting the cultivated plants when they reach the desired maturity and optionally in separating the seeds from the harvested plants.

In the above two methods, the application of the particular herbicide may be made according to the invention before sowing, before emergence and after emergence of the crop.

Advantageously, the enzyme for tolerance to a herbicide is an appropriate EPSPS, and in this case the herbicide is glyphosate or its salts, or the enzyme is an HPPD and the herbicide is chosen from the isoxazoles, in particular isoxafutole, the diketonitriles or the triketones, in particular sulcotrione.

The examples below make it possible to illustrate the invention without seeking to limit its scope.

1. Construction of a Chimeric Gene with a Sequence Encoding an HPPD

The plasmids below are prepared so as to create an expression cassette comprising a maize H3C4 histone promoter combined with the untranslated 5' region of the first intron of the rice actin gene (ActI) described by Mc Elroy D. et al. (Plant Molecular Biology 15: 257–268 (1990)) directing the expression of the gene OTP-HPPD of *Pseudomonas fluorescens*.

pRPA-RD-195

The plasmid pRPA-RD-195 is a derivative of the plasmid pUC-19 which contains a modified multiple cloning site. The complementary oligonucleotides 1 and 2 below are hybridized at 65 C for 5 minutes, followed by a slow cooling down to 30 C over 30 minutes:

```
Oligo 4:5' AGGGCCCCCT AGGGTTTAAA                                          (SEQ ID NO: 4)
           CGGCCAGTCA GGCCGAATTC
    GAGCTCGGTA
CCCGGG-
GATC
           CTCTAGAGTC GACCTGCAGG
           CATGC 3'
```

```
Oligo 5: 5' CCCTGAACCA GGCTCGAGGG                                    (SEQ ID NO: 5)

CGCGCCTTAA TTAAAAGCTT

GCATGCCTGC AGGTCGACTC

TAGAGG 3'
```

The hybridized oligonucleotides are made double-stranded using the Klenow fragment of DNA polymerase I of *E. coli* to extend the 3' ends of each oligo using the standard conditions recommended by the manufacturer (New England Biolabs). The double-stranded oligo obtained is then linked in the plasmid pUC-19 previously digested with the restriction enzymes EcoRI and HindIII and made blunt-ended using the Klenow fragment of DNA polymerase I of *E. coli*. A cloning vector is thus obtained which comprises a multiple cloning site so as to facilitate the introduction of expression cassettes into a plasmid vector of *Agrobacterium tumefaciens* (FIG. 1).

pRPA-RD-2010

Insertion of the sequence "H4A748 promoter-OTP-double mutant EPSPS gene" of pRPA-RD-159 into the plasmid pRPA-RD-195.

The plasmid pRPA-RD-195 is digested with the restriction enzyme SacI and dephosphorylated with calf intestinal alkaline phosphatase (New England Biolabs). The plasmid pRPA-RD-173 (described in patent FR 2,736,926) is digested with the restriction enzyme SacI and the DNA fragment containing the EPSPS gene is purified and linked into the plasmid pRPA-RD-195 prepared above. The clone obtained contains several unique restriction sites flanking the double-mutant EPSPS gene.

pRPA-RD-1002

Creation of an expression cassette OTP-HPPD for use in monocotyledonous plants. The plasmid pRP-P contains the optimized transit peptide (OTP) linked to the HPPD of *Pseudomonas fluorescens* followed by the polyadenylation site of nopaline synthase as described in patent application WO 96/38567. The components of the plasmid pRP-P are the following:

the optimized transit peptide (OTP) described in U.S. Pat. Nos. 5,510,471 and 5,633,448; this OTP consisting of 171 bp of the *Helianthus annuus* ribulose 1,5-bisphosphate carboxylase/oxygenase small subunit transit peptide (Waksman G. et al. 1987. Nucleics Acids Res. 15: 7181) which are followed by the 66 bp of the mature portion of the *Zea mays* ribulose 1,5-bisposphate carboxylase/oxygenase small subunit (Lebrun et al. 1987. Nucleics Acids Res. 15: 4360) which are themselves followed by the 150 bp of the *Zea mays* ribulose 1,5-bisphosphate carboxylase/oxygenase small subunit transit peptide (Lebrun et al. 1987. Nucleics Acids Res. 15: 4360); the combination is therefore 387 bp;

the coding region of the HPPD of *Pseudomonas fluorescens* described in patent application WO 96/38567; and the nopaline synthase (nos) terminator gene (polyadenylation zone of the nos gene isolated from pTi 37, 250 bp; Bevan M. et al. Nucleics Acids Res. 11: 369–385).

Figure 2:
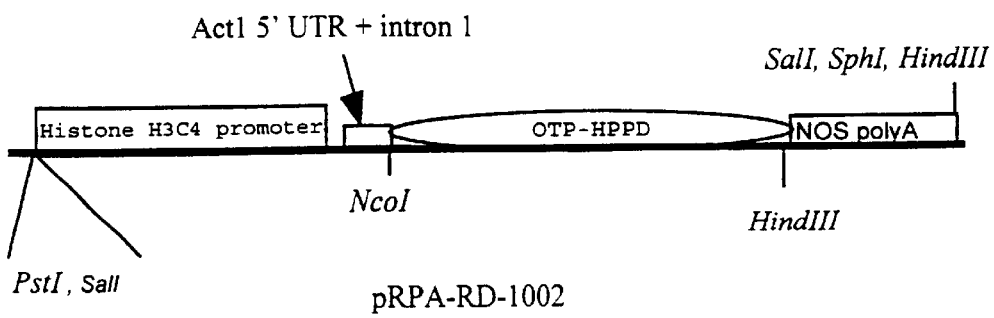
FIG. 2 shows a diagram of the expression cassette OTP-HPPD in plasmid pRPA-RD-1002, which expression cassette comprises the maize H3C4 histone promoter combined with the 5' untranslated region and the first intron of the rice actin gene, the coding region OTP-HPPD and the NOS polyadenylation site.

The plasmid pRP-P is digested with the restriction enzyme BstEII, treated with the Klenow fragment of DNA polymerase I of *E. coli* in order to make the fragment blunt-ended, and followed by digestion with the restriction enzyme NcoI. The DNA fragment obtained, containing the coding region OTP-HPPD about 1.5 kb, is then purified. The plasmid pRPA-RD-2010 obtained above is digested with the restriction enzyme BlpI, treated with the Klenow fragment of DNA polymerase I of *E. coli* in order to obtain a blunt-ended fragment, and then digested with the restriction enzyme NcoI. The DNA fragment obtained, comprising the sequences of the plasmid vector, the H3C4 promoter combined with the untranslated 5' region and the first intron of the rice actin gene, is purified and the NOS polyadenylation site is purified. The two DNA fragments purified are linked so as to create an expression cassette OTP-HPPD comprising the maize H3C4 histone promoter (Brignon et al.) combined with the 5' untranslated region and the first intron of the rice actin gene (ActI) (Act1 5' UTR+intron 1) in order to control the expression of the coding region OTP-HPPD incorporating the NOS polyadenylation site (NOS polyA) (FIG. 2).

2. Construction of a Chimeric Gene with a Sequence Encoding the Double-mutant EPSPS pRPA-RD-1010

Creation of an expression cassette OTP-double mutant EPSPS for use in monocotyledonous plants.

Figure 3:
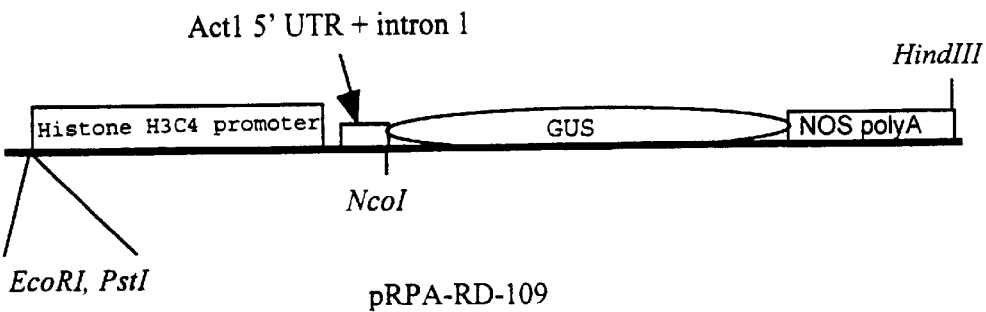
FIG. 3 shows a diagram of a portion of the plasmid pRPA-RD-109 which contains the β-glucuronidase (GUS) gene of E. coli controlled by the maize H3C4 histone promoter combined with the 5' untranslated region and the first intron of the rice actin gene and the NOS polyadenylation site.

The plasmid pRPA-RD-109 contains the β-glucuronidase (GUS) gene of *E. coli* controlled by the maize H3C4 histone promoter (Brignon et al.) combined with the 5' untranslated region and the first intron of the rice actin gene (ActI) described by Mc Elroy D. et al. (Plant Molecular Biology 15: 257–268, 1990). A diagram of this plasmid is represented in FIG. 3. The plasmid pRPA-RD-109 is digested with the restriction enzymes NcoI and EcoRI, and the large DNA fragment (about 5 kb) containing the vector sequence, the GUS gene and the NOS polyadenylation site is purified. The plasmid pRPA-RD-2010 is digested with the restriction enzymes NcoI and EcoRI, and the DNA fragment (about 1.6 kb) containing the H3C4 promoter combined with the 5' untranslated region and the first intron of the rice actin gene (ActI) is purified. The two DNA fragments purified are linked in order to create an expression cassette OTP-double mutant EPSPS comprising the maize H3C4 histone promoter (Brignon et al.) combined with the 5' untranslated region and the first intron of the rice actin gene (ActI) in order to control the expression of the coding region OTP-double mutant EPSPS incorporating the NOS polyadenylation site.

3. Construction of a Chimeric Gene for Tolerance to Phosphinothricin (Bar Gene)

The phosphinothricin acetyl transferase (PAT) encoded by the bar gene is an enzyme which inactivates a herbicide, phosphinothricin (PPT). PPT inhibits the synthesis of glutamine and causes a rapid accumulation of ammonia in the cells, leading to their death (Tachibana et al. 1986).

The plasmid used to introduce the tolerance to phosphinothricin as selection agent is obtained by inserting the chimeric gene pDM 302 into the vector pSP72 of 2462 bp, marketed by Promega Corp. (Genbank/DDBJ database accession number X65332) and containing the gene for resistance to ampicillin.

The plasmid pDM 302 of 4700 bp has been described by Cao, J., et al. Plant Cell Report 11: 586–591 (1992).

The various components of this plasmid are:

the promoter of the rice actin gene described by Mc Elroy D. et al. Plant Molecular Biology 15: 257–268 (1990) consisting of 840 bp;

the first exon of the rice actin gene consisting of 80 bp;

the first intron of the rice actin gene consisting of 450 bp; the region encoding the bar gene of 600 bp excised from the plasmid pIJ41404 described by White J. et al. Nuc. Acids Res. 18: 1862 (1990); the terminator of the nopaline synthase (nos) gene (polyadenylation zone of the nos gene isolated from pTi 37, 250 bp; (Bevan M. et al. Nucleics Acids Res. 11: 369–385).

4. Transformation of Maize Cells

The particle bombardment technique is used to introduce the genetic construct. The plasmids are purified on a Qiagen column and coprecipitated on M10 tungsten particles according to the Klein method (Nature 327: 70–73, 1987).

A mixture of metal particles, of the plasmid pRPA-RD-1002 and of the plasmid of Example 3 which are described above, is then bombarded onto embryogenic maize cells according to the protocol described by Gordon-Kamm, W. J. et al. (*Transformation of Maize Cells and Regeneration of Fertile Transgenic Plants*, The Plant Cell, vol. 2, 603–618, July 1990).

5. Regeneration and Use of the Bar Gene as Selection Agent

The bombarded calli are selected on glufosinate until green sectors appear. The glufosinate-resistant positive calli are then converted to somatic embryos, and then placed under conditions which promote germination according to the operating conditions described by Gordon-Kamm, W. J. et al. (*Transformation of Maize Cells and Regeneration of Fertile Transgenic Plants*, The Plant Cell, vol. 2, 603–618, July 1990). The young plants are transferred to a greenhouse for the production of seeds.

6. Analysis of the Progeny of the Transformed Plants

The transformed plants obtained above are assumed in part to be transgenic, comprising a heterologous gene encoding OTP/HPPD conferring tolerance to isoxazoles such as isoxafutole. These transformed plants produced pollen, which fertilized ovules from a nontransgenic wild-type maize. The seeds obtained are selected on sand after treating with isoxaflutole. The selection protocol is the following:

800 ml of Fontainebleau sand are placed in a tub of sides 15×20 cm. These tubs are then sprinkled with water and kept moist by supplying a nutrient solution consisting of 5 ml of Quinoligo (Quinoline) per liter of water. Twenty maize seeds are placed in the tubs, which are then treated with isoxaflutole by spraying at a rate of 100 g of active material per hectare (300 µg of active material per tub). The tubs are then cultured in a greenhouse. The phytotoxicity is determined 14 [lacuna] after planting. According to the above conditions, the nontransformed plants exhibit 100% phytotoxicity whereas the transformed plants exhibit no phytotoxicity.

A comparative study was carried out with 20 maize lines transformed according to the invention and 20 maize lines transformed with a corresponding gene for which the sequence encoding the first intron of rice actin has been replaced with the sequence encoding the maize adh I intron. After treating by spraying very high doses of isoxafutole at a rate of 200 g of active material per hectare (600 µg of active material per tub), the following results are obtained:

Rice actin intron according to the invention: 8/20 lines are tolerant

Maize adh I intron: 3/20 lines are tolerant

The results above demonstrate that the combination of the maize H3C4 promoter with the first intron of rice actin according to the invention substantially enhances the expression of a protein of interest in transformed monocotyledonous plants compared with the combination of the same maize H3C4 promoter with another intron of the state of the art.

What is claimed is:

1. An isolated DNA sequence comprising, in the direction of transcription, a fragment of the sequence of the maize H3C4 promoter wherein said fragment of the sequence of the maize H3C4 promoter has the sequence shown in SEQ ID NO: 1 and a fragment of the sequence of the first intron of rice actin wherein said fragment of the sequence of the first intran of rice actin has the sequence shown in SEQ ID NO: 2.

2. An isolated DNA sequence comprising the DNA sequence shown in SEQ ID NO: 3.

3. An expression cassette comprising a coding sequence and 5' and 3' heterologous regulatory elements, wherein the 5' regulatory element comprises the isolated DNA sequence according to claim 1, and wherein said expression cassette functions in monocotyledonous plants or plant cells.

4. An expression cassette according to claim 3, wherein the coding sequence is a DNA sequence encoding a protein of interest.

5. The expression cassette according to claim 4, wherein the DNA sequence encoding a protein of interest is a DNA sequence encoding a selectable marker.

6. The expression cassette according to claim 4, wherein the DNA sequence encoding a protein of interest is selected from the group consisting of a DNA sequence encoding a protein that confers herbicide tolerance, a DNA sequence encoding a protein that confers insect tolerance, and a DNA sequence encoding a protein that confers disease tolerance.

7. The expression cassette according to claim 6, wherein the DNA sequence encoding a protein that confers herbicide tolerance is selected from the group consisting of a DNA sequence encoding the Bar gene conferring tolerance to bialophos, a DNA sequence encoding an EPSPS conferring resistance to herbicides having EFSPS as a target, a DNA sequence encoding glyphosate oxidoreductase, and a DNA sequence encoding an HPPD conferring tolerance to herbicides having HPPD as a target.

8. The expression cassette according to claim 7, wherein the DNA sequence encoding a protein that confers herbicide tolerance is a DNA sequence encoding an EPSPS or a DNA sequence encoding an HPPD.

9. The expression cassette according to claim 8, wherein the DNA sequence encoding a protein that confers herbicide tolerance is a DNA sequence encoding an EPSPS.

10. A cloning or expression vector for the transformation of a plant cell or of a plant, which comprises the expression cassette according to claim 3 and at least one replication origin.

11. The cloning or expression vector according to claim 10, which is a plasmid.

12. A method of transforming plant cells, comprising integrating the expression cassette according to claim 3 into the plant cells resulting in transformed plant cells.

13. A plant cell which contains at least one expression cassette according to claim 3.

14. A transformed plant which comprises the plant cell according to claim 13.

15. A transformed plant which is regenerated from a plant cell according to claim 13.

16. A transformed plant produced from the culture of a transformed plant according to claim 14 or the crossing of a transformed plant according to claim 14 with another plant.

17. Seed of the transformed plant according to claim 14.

18. The expression cassette according to claim 9, wherein the DNA sequence encoding an EPSPS is CP4 or a double-mutant EPSPS.

19. A method of controlling weeds in a field comprising weeds and seeds or plants, said weeds or plants each comprising the expression cassette according to claim 7, which method consists in applying to the field a dose of herbicide which is toxic to the weeds but to which the seeds or plants are tolerant.

20. A method of cultivating plants transformed with the expression cassette according to claim 7, which method comprises:

sowing seeds comprising said expression cassette in a field comprising weeds; cultivating plants from the seeds; applying to the field a dose of herbicide which is toxic to the weeds but to which the seeds or plants are tolerant; and harvesting the cultivated plants when they reach maturity.

21. The method according to claim 5, wherein the applying step is before the sowing step, or during or after the sowing step.

22. A transformed plant produced from the crossing of the transformed plant of claim 16.

\* \* \* \* \*